United States Patent
Bara et al.

[11] Patent Number: 5,942,213
[45] Date of Patent: Aug. 24, 1999

[54] WATER-IN-OIL EMULSION STABLE IN THE COURSE OF TIME, WITH SILICONE CONTENT

[75] Inventors: Isabelle Bara, Paris; Myriam Mellul, L'Hay les Roses, both of France

[73] Assignee: L'Oreal, Paris, France

[21] Appl. No.: 08/695,804

[22] Filed: Aug. 12, 1996

Related U.S. Application Data

[63] Continuation-in-part of application No. 08/585,869, Jan. 16, 1996, abandoned, which is a continuation of application No. 08/122,420, Jan. 7, 1994, abandoned.

[30] Foreign Application Priority Data

Jan. 27, 1992 [FR] France .................................. 92 00816

[51] Int. Cl.$^6$ ........................... A61K 7/021; A61K 31/74
[52] U.S. Cl. ........................ 424/63; 424/70.7; 424/78.03
[58] Field of Search .................................. 424/70.17, 63, 424/70.7

[56] References Cited

U.S. PATENT DOCUMENTS

| | | | |
|---|---|---|---|
| 5,217,652 | 6/1993 | Jovanni ..................................... | 424/70 |
| 5,340,570 | 8/1994 | Wong ........................................ | 242/70 |
| 5,344,643 | 9/1994 | Thiel ........................................ | 424/70 |
| 5,658,552 | 8/1997 | Bünning et al. ...................... | 424/70.12 |

FOREIGN PATENT DOCUMENTS

| | | |
|---|---|---|
| 0331833 | 9/1989 | European Pat. Off. . |
| 0374332 | 6/1990 | European Pat. Off. . |
| 2243780 | 11/1991 | United Kingdom . |

*Primary Examiner*—Peter F. Kulkosky
*Attorney, Agent, or Firm*—Nixon & Vanderhye, P.C.

[57] ABSTRACT

Stable water-in-oil emulsion for cosmetic or pharmaceutical use.

This emulsion comprises a fatty phase in a proportion of 15 to 40% consisting of at least one silicone in a proportion of 15 to 40% by weight relative to the total weight of the emulsion, and an aqueous phase containing at least one electrolyte-insensitive aqueous gelling agent, the emulsifying agent of the said emulsion being an alkyl- or alkoxy-dimethicone copolyol of general formula:

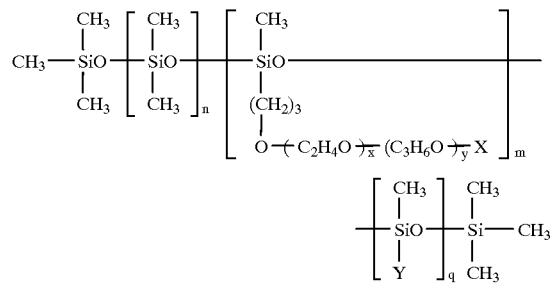

in which:

X is a hydrogen atom or a $C_1$–$C_{16}$ alkyl, $C_1$–$C_{16}$ alkoxy or $C_1$–$C_{16}$ acyl,
Y is a $C_8$–$C_{22}$ alkyl or $C_8$–$C_{22}$ alkoxy radical,
n=0 to 200,
m=1 to 40,
q=1 to 100, the molecular weight of the residue $(C_2H_4O\text{—})_x(C_3H_6O\text{—})_y\text{—}X$ being from 250 to 2000, and x and y being chosen in such a way that the weight ratio of oxyethylene to oxypropylene groups is between 100:0 and 20:80.

Production of stable emulsions having excellent cosmetic properties.

16 Claims, No Drawings

WATER-IN-OIL EMULSION STABLE IN THE COURSE OF TIME, WITH SILICONE CONTENT

This is a Continuation-in-Part of prior Application Ser. No. 585,869 filed Jan. 16, 1996 now abandoned which is a Rule 60 Continuation of Application Ser. No. 08/122,420, filed Jan. 7, 1994 now abandoned.

The present invention relates to water-in-oil (W/O) emulsions having a high silicone content.

Such W/O emulsions are useful in cosmetics, in particular for their capacity to form films on the surface of the skin which are effective in preventing transepidermal water loss and which offer good resistance to contamination by microorganisms.

It is known that, the greater the silicone oil content, the more difficult it is to obtain a W/O emulsion which is stable not only over time but also when subjected to large temperature variations.

In spite of the considerable research in this field, it has not been possible to develop W/O emulsions with good stability having a high silicone oil content.

These stability problems can, according to U.S. Pat. No. 4,698,178, be at least partially solved by the use of a novel class of silicone-based surfactants.

However, while this patent states that, by the use of these surfactants, W/O emulsions can be obtained in which the proportion of silicone oil can amount to 8 to 50%, these are illustrated only by examples containing at most 8.5% of silicone oil.

According to this patent, the stability is obtained not only by means of the silicone-based surfactants described, but also by the use, on the one hand of polyols for low temperatures, and on the other hand of electrolytes or metal soaps for high temperatures.

Stabilization of W/O emulsions is achieved in a known manner using stabilizers of the fatty phase, in particular with fat-soluble polymers, with waxes or with organically modified clays, these latter being described in EP-A-0,009,404 and EP-A-0,331,833.

It has now been discovered, unexpectedly and surprisingly, that, by the use of electrolyte-insensitive gelling agents in the aqueous disperse phase in combination with an emulsifier of the alkyl- or alkoxydimethicone copolyol type, it was possible to overcome the drawbacks mentioned above and to obtain W/O emulsions having good stability over time and to temperature variations.

The subject of the present invention is hence a stable water-in-oil emulsion, for cosmetic or pharmaceutical use, characterized in that it comprises a fatty phase in a proportion of 15 to 40% consisting of at least one silicone in a proportion of 15 to 40% by weight relative to the total weight of the emulsion, and an aqueous phase containing at least one electrolyte-insensitive aqueous gelling agent, the emulsifying agent of the said emulsion being an alkyl- or alkoxydimethicone copolyol of general formula:

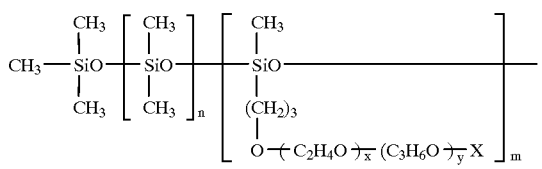

-continued

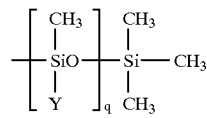

in which:
X is a hydrogen atom or a $C_1$–$C_{16}$ alkyl, $C_1$–$C_{16}$ alkoxy or $C_1$–$C_{16}$ acyl,
Y is a $C_8$–$C_{22}$ alkyl or $C_8$–$C_{22}$ alkoxy radical,
n=0 to 200,
m=1 to 40,
q=1 to 100,
the molecular weight of the residue $(C_2H_4O$—$)_x$ $(C_3H_6O$—$)_y$—X being from 250 to 2000, and x and y being chosen in such a way that the weight ratio of oxyethylene to oxypropylene groups is between 100:0 and 20:80.

The W/O emulsion according to the present invention is free from water-swellable clay mineral and cationic surfactants.

The W/O emulsion according to the invention fully meets the stability standards, namely:
resistance to the test of centrifugation at 4000 rpm for 1 hour,
resistance to ageing at room temperature for 3 months as well as at 45° C. and +4° C., and
resistance to 8 successive cycles of 8 hours each in which the temperatures range from −25° C. to +47° C.

The emulsion according to the invention satisfies the following criteria:
it has, and retains during these tests, a homogeneous and stable macroscopic and microscopic appearance (finely dispersed globules, absence of coagulation), and
its viscosity is constant over time and is between 0.1 Pa.sec and 10 Pa.sec, and preferably between 0.2 Pa.sec and 6 Pa.sec.

The emulsions according to the invention possess, moreover, good qualities in relation to the sensations they produce, in particular a great ease of application, comfort, smoothness, good mattness, uniformity and hold.

The use of aqueous gelling agents according to the invention imparts rheological properties of thickening and/or thixotropy to the aqueous disperse phase, and hence enables a more stable emulsion to be obtained. The emulsions thus stabilized make it possible to dispense with preservatives. In effect, surprisingly, it was found that the stabilized emulsions possessed excellent bacteriostatic and/or bacteriocidal properties.

According to the invention, it is possible to use as aqueous gelling agent all those whose good functioning is independent of the ionic character of the medium.

Preferably, organic aqueous gelling agents chosen from the following are employed:
polysaccharides such as cellulose derivatives (carboxymethylcellulose, hydroxypropylmethylcellulose), natural gums such as xanthan, guar and carob gums, scleroglucans and chitin or chitosan derivatives,
proteins or their hydrolysates, such as keratin, gelatin and collagen,
acrylic and methacrylic derivatives such as glycerol polyacrylate (including the product sold by the company SEDERMA under the name "LUBRAJEL®") and ammonium acrylate copolymer (including the product sold by the company HOECHST under the name "PAS 5161®"), polyethylene glycols (PEG) such as the products sold by the company UNION CARBIDE under the name "CARBOWAX®", and mixtures of these.

According to the invention, the aqueous gelling agent is present in a proportion of between 0.1 and 5%, and preferably between 0.3 and 2%, by weight of active substance relative to the total weight of the emulsion.

The silicone which can be used according to the invention can be an optionally functionalized linear polydiorganosiloxane or a cyclic polydiorganosiloxane, a methylorganopolysiloxane or a mixture of these.

The optionally functionalized linear polydiorganosiloxanes which can be used according to the invention correspond to the following general formula:

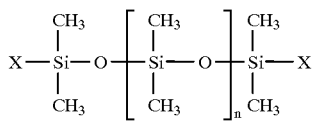

in which:

X is —CH$_3$ or OH, and n is 0 to 5000.

Among these, there may be mentioned, in particular, the products sold under the name "AK®" by the company WACKER, "SF®" by the company GENERAL ELECTRIC and "ABIL®" by the company GOLDSCHMIDT, such as the product "ABIL 10®", or alternatively the products sold under the name "Q2 1401®" and "Q2 1403®" by the company DOW CORNING.

As cyclic polydiorganosiloxanes according to the invention, it is possible to use, alone or mixed, cyclomethicones of formula:

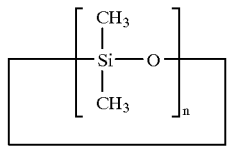

in which:

n is an integer from 3 to 8.

Among especially preferred cyclomethicones, cyclotetradimethylsiloxane (n=4), cyclopentadimethylsiloxane (n=5) and cyclohexadimethylsiloxane (n=6) may be mentioned.

It is possible, in particular, to use the products sold under the names "DC FLUID 244®", "DC FLUID 245®", "DC FLUID 344®" and "DC FLUID 345®" by the company DOW CORNING.

Other cyclomethicones which can be used according to the invention are those sold under the names "ABIL K4®" by the company GOLDSCHMIDT; under the names "SILBIONE 70045 V2®" and "SILBIONE HUILE 70045®" by the company RHONE POULENC; and also under the names "VOLATILE SILICONE 7158®" and "VOLATILE SILICONE 7207®" by the company UNION CARBIDE.

The organopolysiloxanes according to the invention can be alkyl-, alkoxy- or phenyldimethicones such as, for example:

(a) an alkoxydimethicone having one of the following formulae:

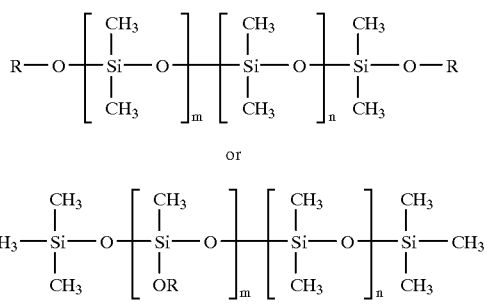

in which formulae:

R is a C$_6$ to C$_{30}$ alkyl radical, m is 1 to 100 and n is 0 to 100.

The product sold under the name "ABIL WAX 2440®" by the company GOLDSCHMIDT may be mentioned in particular.

(b) an alkyldimethicone having one of the following formulae:

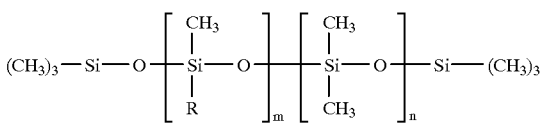

in which:

R is a C$_6$ to C$_{30}$ alkyl radical, m is 1 to 100 and n is 0 to 100, or

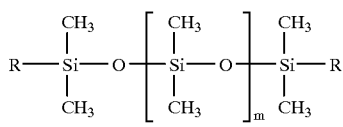

in which:

R is a C$_6$ to C$_{30}$ alkyl radical, m is 1 to 100.

(c) a phenyldimethicone having the following formula:

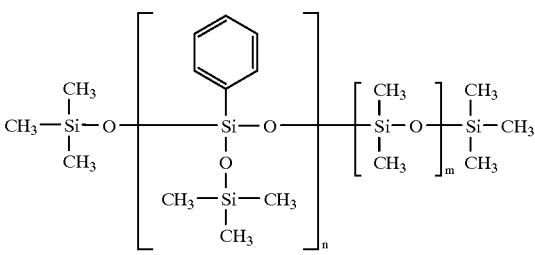

in which:

m is 0 to 100 and n is 1 to 400, or the following formula:

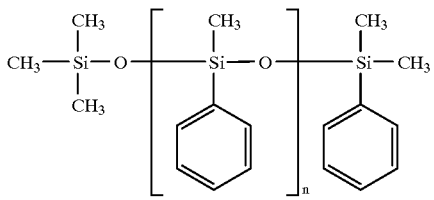

in which:
n is 0 to 400.

The organosiloxanes which can be used according to the invention can also be trimethylsiloxy silicates (CTFA) containing units:

$(R)_2SiO_{2/2}$; $RSiO_{3/2}$ and $RSiO_{4/2}$

R being a $C_1$ to $C_6$ lower alkyl radical or a phenyl radical.

As stated above, the silicone used according to the invention is present in a proportion of between 15 and 40%, but preferably between 15 and 30%, by weight relative to the total weight of the emulsion.

When the silicone is an optionally functionalized polydiorganosiloxane, it is preferably present in a proportion of between 0.1 and 15% by weight relative to the total weight of the emulsion.

When the silicone is a cyclic polydiorganosiloxane, it is preferably present in a proportion of between 1 and 30% by weight relative to the total weight of the emulsion.

When the silicone is an organopolysiloxane, it is preferably present in a proportion of between 0.1 and 10% relative to the total weight of the emulsion.

The fatty phase of the W/O emulsion according to the invention can comprise one or more non-silicone oil(s) in a proportion of between 0.1 and 26%, and preferably between 0.1 and 15%, by weight relative to the total weight of the emulsion.

As non-silicone oil, there may be mentioned any fluid oil (or mixture of oils) which is stable at the temperature at which cosmetic and pharmaceutically or cosmetically acceptable products are normally used, such as vegetable or animal oils, mineral or synthetic oils and fatty acid triglycerides.

Among modified or unmodified vegetable or animal oils, there may be mentioned, for example, sweet almond oil, avocado oil, castor oil, olive oil, jojoba oil, sunflower oil, wheat germ oil, sesame oil, groundnut oil, grape pip oil, soya bean oil, rapeseed oil, safflower oil, coconut oil, maize oil, hazelnut oil, shea butter, palm oil, kernel oil and calophyllum oil.

Among mineral oils, liquid paraffin may be mentioned, for example.

Among fatty acid triglycerides, caprylic/capric triglycerides, $C_{10}$ to $C_{18}$ fatty acid triglycerides and $C_{12}$ to $C_{18}$ fatty acid triglycerides may be mentioned.

The surfactant or emulsifier as defined above is used according to the invention in a proportion of between 0.5 and 10%, and preferably between 2 and 6%, by weight relative to the total weight of the emulsion, and has been shown to be less irritant than some other surfactants.

Among commercially available products which can contain all or part of the alkyldimethicone copolyols which can be used according to the invention as emulsifier, there may be mentioned, in particular, those sold under the name "ABIL WE09®" or "ABIL WS08®" by the company GOLDSCHMIDT, "Q2 5200®" by the company DOW CORNING and "218 1138®" by the company GENERAL ELECTRIC.

According to a particular embodiment of the invention, it is possible to employ an additional surfactant such as a glycerol ester or ether and/or a dispersion of oxyethylenated polydimethylsiloxane in a cyclodimethylsiloxane ("Q3225C®" of the company DOW CORNING) having an HLB of between 2 and 7 and present in a proportion of between 0.01 and 5% by weight relative to the total weight of the emulsion.

Among additional surfactants of this type, there may be mentioned glycerol esters or ethers, in particular the isostearic acid and/or succinic acid ester and the ether of decyltetradecyl alcohol. There may be mentioned, for example, the product sold by the company DYNAMIT NOBEL under the name "IMWITOR 780®", which is an isostearyl diglyceryl succinate.

Moreover, some products consisting of a mixture of alkyldimethicone copolyol of the formula given above and an additional surfactant of the type mentioned above are commercially available.

There may be mentioned, in this connection, the product sold by the company GOLDSCHMIDT under the name "ABIL WE09®", which contains an alkyldimethicone copolyol possessing a weight ratio of oxyethylene to oxypropylene groups of between 100:0 and 20:80 combined with a glycerol isostearate and hexyl laurate.

If desired, and in order to modify the texture and the cosmetic properties of the emulsion according to the invention, the fatty phase can contain at least one oily gelling agent chosen from:

metal salts of $C_8$ to $C_{22}$ fatty acids, such as aluminum stearate and aluminum magnesium hydroxystearate, esters of $C_8$ to $C_{22}$ fatty acids and glycol, mixtures of $C_{14}$ to $C_{32}$ fatty alcohols, silicone waxes of the alkyldimethicone or alkoxydimethicone type, organically modified clays, in particular bentone, cholesterol derivatives, in particular hydroxycholesterol, and mixtures of these.

The oily gelling agents can be present in a highly variable proportion, depending on the desired texture. However, in most cases, they are present in a proportion of between 0.1 and 10% by weight relative to the total weight of the emulsion.

According to the invention, the fatty phase can also contain pigments, where appropriate coated with hydrophilic or hydrophobic substances such as:

polyethylene, lecithin, an amino acid salt such as aluminum acylglutamate, poly(methyl methacrylate), triisostearoyl titanate, and collagen.

Among coated pigments, the pigments sold under the name "COVASIL®" by the company WACKER (pigments with triisostearoyl titanate) may be mentioned in particular.

The pigments thus coated may be incorporated in the emulsion according to the invention in a proportion of between 0.1 and 15% by weight relative to the total weight of the emulsion.

Among other fat-soluble adjuvants which can be incorporated in the fatty phase, lipophilic UV screening agents, lipophilic vitamins, antioxidants and perfumes may be mentioned.

The aqueous phase can also contain adjuvants commonly used in cosmetic W/O emulsions. There may be mentioned, for example, lubricants, texturing agents of the polyether silicone wax type, hydrating agents such as glycerol and propylene glycol, proteins or their hydrolysates such as those of collagen and elastin, hydrophilic UV screening agents and polysaccharides, as well as electrolytes such as NaCl or $MgSO_4$.

The emulsion according to the invention can also incorporate fillers of vegetable, mineral or synthetic origin, especially starch powder, colloidal silica, nylon powder (Orgasol) and talc.

One of the main advantages resulting from the very effective stabilization of the emulsion according to the invention with the gelling agents described above is the possibility of incorporating substances which are renowned for their destabilizing effect on W/O emulsions, in particular those having an ionic character.

There may be mentioned, in particular, UV screening agents such as benzophenone-4 and some active principles such as trace elements and biological derivatives. Among trace elements, magnesium gluconate may be mentioned, and among biological derivatives, hydrolysates of serum protein of animal origin and sodium pyrrolidonecarboxylate may be mentioned.

The emulsions according to the invention may be prepared by any conventional process.

However, it is preferable to obtain the emulsion in the following manner: the fatty phase containing the emulsifier is heated to a temperature sufficient to melt all the constituents, preferably between 20 and 95° C., and the desired fat-soluble adjuvants are incorporated.

Then, with vigorous stirring, for example using a MORITZ type stirrer, the aqueous phase containing the gelling agent, brought to a temperature of between 20 and 95° C. and in which all the desired water-soluble adjuvants have previously been incorporated, is added to the molten fatty phase.

The emulsions according to the invention can be in the form of a white or tinted cream or in the form of a makeup foundation, mascara, blusher or lip makeup product. They keep well even in the absence of a preservative.
examples which follow without, however, limiting it.

EXAMPLE 1

White Cream

| Fatty phase A: | |
| --- | --- |
| Alkyldimethicone copolyol "WE09" of the company GOLDSCHMIDT | 5% |
| MIGLYOL 823 ® of the company DYNAMIT NOBEL | 4% |
| Glycerol ester IMWITOR 780K ® of the company DYNAMIT NOBEL | 2% |
| Silicone Q2 1401 ® of the company DOW CORNING | 0.5% |
| Volatile Silicone FLUID 245 ® of the company DOW CORNING | 18.5% |
| Aqueous phase B: | |
| Poly(ammonium acrylate) | 1% |
| Glycerol | 15% |
| $MgSO_4$ | 0.7% |
| Preservative | QS |
| Water | 53.3% |

The white cream is obtained in the following manner: the phase B is heated to a temperature of approximately 90° C. and added in several portions to the phase A brought to the same temperature. Mixing is performed using a Moritz type turbo-mixer at a speed of approximately 3000 rpm.

The cream obtained is attractive in appearance, shiny and slightly translucent, has a pleasant feel and is smooth, non-tacky and cool.

EXAMPLE 2

Makeup Foundation

| Phase A: | |
| --- | --- |
| Alkyldimethicone copolyol WE90 ® of the company GOLDSCHMIDT | 5% |
| Alkyldimethicone ABIL WAX 9810 ® of the company GOLDSCHMIDT | 2% |
| Silicone ABIL 10 ® of the company GOLDSCHMIDT | 9% |
| Titanium oxides coated with lipoamino acids of the company MAPRECOS | 4.12% |
| Iron oxides coated with lipoamino acids of the company MAPRECOS | 0.88% |
| Volatile silicone FLUID 245 ® of the company DOW CORNING | 13.5% |
| Phase B: | |
| Carboxymethylcellulose | 0.5% |
| Glycerol | 14% |
| Polyethylene glycol-20 of molecular weight 1000, CARBOWAX 1000 ® of the company UNION CARBIDE | 1.7% |
| $MgSO_4$ | 0.7% |
| Preservative | 0.5% |
| Water | 48.1% |

The makeup foundation is obtained in the following manner: the whole of the phase A is homogenized with a Moritz type turbo-mixer at 90° C. and at a speed of approximately 3000 rpm.

The phase B is then heated to 90° C. and introduced in several portions into the phase A with vigorous stirring.

The makeup foundation obtained after cooling possesses a very attractive appearance and good cosmetic qualities.

EXAMPLE 3

Makeup Foundation

| Phase A: | |
| --- | --- |
| Alkyldimethicone copolyol WE09 ® of the company GOLDSCHMIDT | 5% |
| Squalane | 4.4% |
| Alkoxydimethicone ABIL WAX 2440 ® of the company GOLDSCHMIDT | 1% |
| Mixture of $C_{14}$ to $C_{22}$ fatty alcohols, NAFOL ® of the company CONDEA | 1.1% |
| Paraffin | 1.2% |
| Hydrogenated castor oil | 0.8% |
| Collagen-coated pigments | 5% |
| Volatile silicone FLUID 245 ® of the company DOW CORNING | 8% |
| Silicone Q2 1403 ® of the company DOW CORNING | 4% |
| Phase B: | |
| Glycerol | 5% |
| Polyethylene glycol-20 CARBOWAX 1000 ® | 1.7% |
| Polyethylene glycol-8 CARBOWAX 400 ® | 3% |
| $MgSO_4$ | 0.7% |
| Preservative | QS |
| Water | 59.1% |

This makeup foundation is obtained in the same manner as for Example 2.

EXAMPLE 4

White Cream

| Phase A: | |
|---|---|
| Alkyldimethicone copolyol WE 09 ® of the company GOLDSCHMIDT | 2% |
| Volatile silicone FLUID 245 ® of the company DOW CORNING | 17% |
| MIGLYOL 812 ® of the company DYNAMIT NOBEL | 4% |
| Glycerol ester IMWITOR 780 K ® of the company DYNAMIT NOBEL | 1% |
| Silicone Q2 1403 ® of the company DOW CORNING | 4% |
| Phase B: | |
| Glycerol | 15% |
| Ammonium acrylate copolymer | 1% |
| MgSO$_4$ | 0.7% |
| Preservative | QS |
| Water | 55.3% |

This cream is obtained in the same manner as for Example 1.

EXAMPLE 5

White Cream

| Phase A: | |
|---|---|
| Alkyldimethicone copolyol WE 09 ® of the company GOLDSCHMIDT | 2% |
| Volatile silicone FLUID 245 ® of the company DOW CORNING | 12% |
| Silicone Q2 1401 ® of the company DOW CORNING | 4% |
| MIGLYOL 812 ® of the company DYNAMIT NOBEL | 2% |
| Glycerol ester IMWITOR 780 K ® of the company DYNAMIT NOBEL | 2% |
| Mixed aluminum and magnesium salt of fatty acids, GILUGEL SIL ® of the company GIULINI CHEMIE | 3% |
| Phase B: | |
| Glycerol | 15% |
| Ammonium acrylate copolymer PAS 516 ® of the company HOECHST | 0.5% |
| MgSO$_4$ | 0.7% |
| Preservative | QS |
| Water | 55.8% |

This cream is obtained in the same manner as for Example 1.

EXAMPLE 6

White Cream

| Phase A: | |
|---|---|
| Alkyldimethicone WE 09 ® of the company GOLDSCHMIDT | 5% |
| Volatile silicone FLUID 245 ® of the company DOW CORNING | 15% |
| MIGLYOL 812 ® of the company DYNAMIT NOBEL | 4% |
| Silicone Q2 1401 ® of the company DOW CORNING | 4% |
| Glycerol ester IMWITOR 780 K ® | 2% |
| Preservative | QS |
| Phase B: | |
| MgSO$_4$ | 0.70% |
| Sulphonic keratin | 2% |
| Water | 67.3% |

This cream is obtained in the same manner as in Example 1.

EXAMPLE 7

White Cream

| Phase A: | |
|---|---|
| Alkyldimethicone WE 09 ® of the company GOLDSCHMIDT | 5% |
| Volatile silicone FLUID 245 ® of the company DOW CORNING | 15% |
| MIGLYOL 812 ® of the company DYNAMIT NOBEL | 4% |
| Silicone Q2 1401 ® of the company DOW CORNING | 4% |
| Glycerol ester IMWITOR 780 K ® | 2% |
| Preservative | QS |
| Phase B: | |
| MgSO$_4$ | 0.7% |
| Hydroxypropylmethylcellulose | 0.3% |
| Water | 69% |

EXAMPLE 8

Makeup Foundation

| Phase A: | |
|---|---|
| Alkyldimethicone WE 09 ® of the company GOLDSCHMIDT | 5% |
| Volatile silicone FLUID 245 ® of the company DOW CORNING | 15% |
| MIGLYOL 812 ® of the company DYNAMIT NOBEL | 2% |
| Silicone Q2 1403 ® of the company DOW CORNING | 4% |
| Silicone-coated titanium oxides of the company WACKER | 1.43% |
| Silicone-coated iron oxides of the company WACKER | 5% |
| Phase B: | |
| MgSO$_4$ | 0.7% |
| Glycerol | 15% |
| Carboxymethylcellulose | 0.5% |
| Water | 51.37% |

This composition keeps well from a bacteriological standpoint even though it does not contain a preservative.

EXAMPLE 9

Fluid Makeup Foundation

| Phase A: | |
|---|---|
| Alkyldimethicone WE 09 ® of the company GOLDSCHMIDT | 10% |
| Cyclopentadimethylsiloxane D5 ® of the company DOW CORNING | 30% |
| Silicone-coated titanium oxide of the company WACKER | 4.8% |
| Silicone-coated black iron oxide of the company WACKER | 0.22% |
| Silicone-coated red iron oxide of the company WACKER | 0.25% |
| Silicone-coated yellow iron oxide of the company WACKER | 1.43% |
| Nylon powder ORGASOL ® of the company ATOCHEM | 5% |
| Phase B: | |
| MgSO$_4$ | 1% |
| Carboxymethylcellulose | 0.5% |
| Polyether silicone wax SLM 23008 ® of the company WACKER | 3% |
| Polyethylene glycol-20 CARBOWAX 1000 ® | 2% |
| Polyethylene glycol-8 CARBOWAX 400 ® | 3% |
| Preservative | 0.3% |
| Water qs | 100% |

The makeup foundation is fluid, spreads easily and leaves the skin very uniform, matt, natural and smooth.

EXAMPLE 10

Pliant Silicone-Based W/O Makeup foundation

| Phase A: | |
|---|---|
| Alkyldimethicone WE 09 ® of the company GOLDSCHMIDT | 5% |
| Cyclopentadimethylsiloxane D5 ® of the company DOW CORNING | 28% |
| Polyphenylsiloxane RP761 ® of the company RHONE POULENC | 0.3% |
| Al Mg hydroxystearate suspended in cyclomethicone, MULTIGEL SIL5 ® the company GIULINI CHEMIE | 6% |
| Silicone-coated titanium oxide of the company WACKER | 4.8% |
| Silicone-coated black iron oxide of the company WACKER | 0.22% |
| Silicone-coated red iron oxide of the company WACKER | 0.55% |
| Silicone-coated yellow iron oxide of the company WACKER | 1.43% |
| Microbeads of silicone-based resin TOSPEARL 108 ® | 6% |
| Phase B: | |
| MgSO$_4$ | 1% |
| Carboxymethylcellulose | 0.3% |
| Polyethylene glycol-8 CARBOWAX 400 ® | 2% |
| Preservative | 0.3% |
| Water qs | 100% |

The makeup foundation takes the form of a very fine, pliant cream. After application, the skin is smooth and matt.

We claim:

1. A cosmetic or pharmaceutical homogeneous water-in-oil emulsion of improved stability which is free of water-swellable clay mineral and cationic surfactants and has a viscosity of 0.1 Pa.sec to 10 Pa.sec, said emulsion containing:

(a) from 15 to 40 percent by weight based on the total weight of said emulsion of a fatty phase containing a silicone selected from the group consisting of an optionally functionalized linear polyorganosiloxane, a cyclic polydiorganosiloxane, an organosiloxane and mixtures thereof, in an amount ranging from 15 to 40 percent by weight based on the total weight of said emulsion, (b) an aqueous phase containing an organic aqueous gelling agent being insensitive to electrolytes selected from the group consisting of a polysaccharide, a protein, a protein hydrolysate, an acrylic or methacrylic polymers, and a mixture thereof, said organic aqueous gelling agent being present in an amount ranging from 0.1 to 5 percent by weight based on the total weight of said emulsion, and (c) from 0.5 to 10 percent by weight based on the total weight of said emulsion of an emulsifying agent having the formula

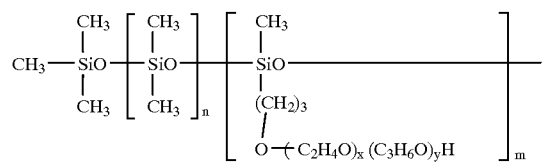

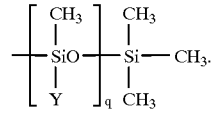

wherein

X is hydrogen, $C_1$–$C_{16}$ alkyl, $C_1$–$C_{16}$ alkoxy or $C_1$–$C_{16}$ acyl, Y is $C_8$–$C_{22}$ alkyl or $C_8$–$C_{22}$ alkoxy, n=0 to 200, m=1 to 40, q=1 to 100, the molecular weight of the residue $(C_2H_4O)_x(C_3H_6O)_yX$ ranging from 200 to 2000, and x and y are selected such that the weight ratio of the oxyethylene to oxypropylene groups is between 100:0 and 20:80; said emulsion meeting the stability standard of resistance to ageing for 3 months at 45° C. and 4° C.

2. The emulsion of claim 1 having a viscosity ranging from 0.2 Pa.sec. to 6 Pa.sec.

3. The emulsion of claim 1 wherein said linear polydiorganosiloxane has the formula

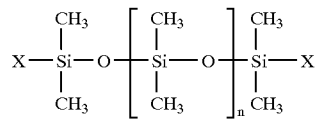

wherein x is —CH$_3$ or OH and n=0 to 5000.

4. The emulsion of claim 1 wherein said cyclic polydiorganosiloxane has the formula

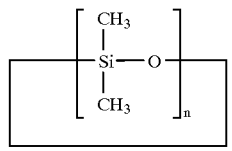

wherein n is an integer ranging from 3 to 8.

5. The emulsion of claim 1 wherein said organosiloxane is selected from the group consisting of an alkyldimethicone, an alkoxydimethicone and a phenyldimethicone.

6. The emulsion of claim 1 wherein said fatty phase also contains a non-silicone oil in an amount ranging from 0.1 to 25 percent by weight based on the total weight of said emulsion.

7. The emulsion of claim 1 wherein said emulsifying agent is present in an amount ranging from 2 to 6 percent by weight based on the total weight of said emulsion.

8. The emulsion of claim 1 wherein said fatty phase contains an oily gelling agent selected from the group consisting of a metal salt of a $C_8$ to $C_{22}$ fatty acid, an ester of a fatty acid and glycol, a mixture of $C_{14}$ to $C_{32}$ fatty alcohols, a silicone wax, a cholesterol derivative and a mixture thereof.

9. The emulsion of claim 8 wherein said oily gelling agent is present in an amount ranging from 0.1 to 10 percent by weight based on the total weight of said emulsion.

10. The emulsion of claim 1 wherein said emulsion also contains a member selected from the group consisting of a glycerol ester, a glycerol ether and a dispersion of oxyethylenated polydimethylsiloxane in a cyclodimethylsiloxane having a HLB between 2 and 7, present in an amount ranging from 0.01 to 5 percent by weight based on the total weight of said emulsion.

11. The emulsion of claim 1 wherein said fatty phase also contains a fat-soluble adjuvant selected from the group consisting of a lipophilic UV screening agent, a lipophilic vitamin, an antioxidant and a perfume.

12. The emulsion of claim 1 wherein said aqueous phase also contains a water-soluble substance selected from the group consisting of a hydrating agent, a lubricant, a texturing agent, a hydrophilic UV screening agent, a trace element and a biological derivative.

13. The emulsion of claim 1 which is free from a preservative.

14. The emulsion of claim 1 which also contains a pigment.

15. The emulsion of claim 1 wherein said pigment is coated with a hydrophilic or hydrophobic substance.

16. The emulsion of claim 15 wherein said hydrophilic or hydrophobic substance is selected from the group consisting of polyethylene, lecithin, an amino acid salt, poly(methyl methacrylate), triisostearoyl titanate and collagen.

* * * * *